United States Patent
Schimperna et al.

(10) Patent No.: US 9,000,170 B2
(45) Date of Patent: Apr. 7, 2015

(54) PROCESS FOR THE PREPARATION OF TETRACARBOXYNAPHTHALENEDIIMIDE COMPOUNDS DISUBSTITUTED WITH HETEROARYL GROUPS

(71) Applicant: ENI S.P.A., Rome (IT)

(72) Inventors: Guiliana Schimperna, Novara (IT); Andrea Pellegrino, Trecate (IT); Stefano Chiaberge, Turin (IT); Gabriele Bianchi, L'Aquila (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 14/386,131

(22) PCT Filed: Mar. 18, 2013

(86) PCT No.: PCT/IB2013/052153
§ 371 (c)(1),
(2) Date: Sep. 18, 2014

(87) PCT Pub. No.: WO2013/140328
PCT Pub. Date: Sep. 26, 2013

(65) Prior Publication Data
US 2015/0051398 A1    Feb. 19, 2015

(30) Foreign Application Priority Data

Mar. 19, 2012 (IT) .............................. MI2012A0417

(51) Int. Cl.
*C07D 471/08* (2006.01)
*C07D 333/10* (2006.01)
*C07D 471/06* (2006.01)

(52) U.S. Cl.
CPC .................................. *C07D 471/06* (2013.01)

(58) Field of Classification Search
USPC ............................................. 546/66; 549/29
See application file for complete search history.

(56) References Cited

PUBLICATIONS

Piyakulawat, P. et al.: Low band copolymer containing naphthalene-1,4,5,8-tetracarboxylic bisamide: synthesis, properties and organic solar cell applications. Synthetic Metals, vol. 161, pp. 1238-1244, 2011.*
International Search Report issued in PCT/IB2013/052153 dated Jun. 28, 2013.
Neil A. Strotman et al.; "Highly Regioselective Palladium-Catalyzed Direct Arylation of Oxazole at C-2 or C-5 with Aryl Bromides, Chlorides, and Triflates"; Organic Letters, 2010, vol. 12, No. 16, pp. 3578-3581.
Sheshanath V. Bhosale et al.; "The synthesis of novel core-substituted naphthalene diimides via Suzuki cross-coupling and their properties"; New J. Chem, 2009, 33, pp. 2409-2413.
Phimwipha Piyakulawat et al; "Low band gap copolymer containing naphthalene-1,4,5,8-tetracarboxyic bisimide: Synthesis, properties and organic solar cell applications"; Synthetic Metals, 161 (2011), pp. 1238-1244.
Mathieu Parisien et al.; "Direct Arylation Reactions Catalyzed by $Pd(OH)_2$/C: Evidence for a Soluble Palladium Catalyst"; J. Org. Chem., 2005, 70, pp. 7578-7584.
Fumitoshi Shibahara et al.; "Direct Arylation of Simple Azoles Catalyzed by 1, 10-Phenanthroline Containing Palladium Complexes: An Investigation of C4 Arylation of Azoles and the Synthesis of Triarylated Azoles by Sequential Arylation"; J. Org. Chem., 2011, 76, pp. 2680-2693.

* cited by examiner

*Primary Examiner* — Charanjit Aulakh
(74) *Attorney, Agent, or Firm* — Oblon, McClelland, Maier & Neustadt, L.L.P.

(57) ABSTRACT

A process for the preparation of a tetracarboxynaphthalenediimide compound disubstituted with heteroaryl groups having general formula (I), comprising the reaction of at least one disubstituted N,N'-dialkyl-1,5,8-tetracarboxynaphthalenediimide with at least one heteroaryl compound. Said tetracarboxynaphthalenediimide compound disubstituted with heteroaryl groups can be advantageously used as monomer in the synthesis of semiconductor polymers which can be advantageously used in the construction of organic field effect transistors (OFET) or of organic thin film transistors (OTFT).

20 Claims, No Drawings

PROCESS FOR THE PREPARATION OF TETRACARBOXYNAPHTHALENEDIIMIDE COMPOUNDS DISUBSTITUTED WITH HETEROARYL GROUPS

The present invention relates to a process for the preparation of a tetracarboxynaphthalenediimide compound disubstituted with heteroaryl groups, comprising the reaction of at least one disubstituted N,N'-dialkyl-1,4,5,8-tetracarboxynaphthalenediimide with at least one heteroaryl compound.

Said tetracarboxynaphthalenediimide compound disubstituted with heteroaryl groups can be advantageously used as monomer in the synthesis of semiconductor polymers which can be advantageously used in the construction of organic field effect transistors (OFET) or of organic thin film transistors (OTFT). Furthermore, said tetracarboxynaphthalenediimide compound disubstituted with heteroaryl groups can be advantageously used as monomer in the synthesis of semiconductor polymers which can be advantageously used in the construction of photovoltaic devices such as, for example, photovoltaic cells, photovoltaic modules, solar cells, solar modules, on both rigid and flexible supports.

N,N'-dialkyl-1,4,5,8-tetracarboxynaphthalenediimide compounds (NDIs) are at present of great interest for their physical and electronic properties.

In particular, (co)polymers comprising units deriving from said N,N'-dialkyl-1,4,5,8-tetracarboxy-naphthalenediimide compounds (NDIs) can be advantageously used in the construction of organic field effect transistors (OFET) or of organic thin film transistors (OTFT) and in the construction of photovoltaic devices such as, for example, photovoltaic cells, photovoltaic modules, solar cells, solar modules, on both rigid and flexible supports.

It is known that N,N'-dialkyl-1,4,5,8-tetracarboxy-naphthalenediimide compounds (NDIs) have very interesting characteristics such as, for example, a good thermal stability, good properties as electron-acceptor compounds, a good processability in organic solvents normally used in the construction of the above-mentioned transistors or of the above-mentioned photovoltaic devices.

It is also known that the substituents present on the imide nitrogen of said N,N'-dialkyl-1,4,5,8-tetracarboxynaphthalenediimide compounds (NDIs) can considerably influence the molecular packing, the solubility in the above-reported organic solvents, the morphology of the thin films that comprise them.

Furthermore, said N,N'-dialkyl-1,4,5,8-tetracarboxynaphthalenediimide compounds (NDIs) have good electronic properties such as, for example, a strong π-π interaction and consequently, when used in the construction of photovoltaic devices, for example photovoltaic cells, they have a short intermolecular distance and, in particular, optimum charge transport properties.

It is also known that said electronic properties can be modulated by introducing different substituents on the tetracaboxynaphthalenediimide nucleus.

It is known, for example, that (co)polymers comprising units deriving from tetracaboxy-naphthalenediimide compounds disubstituted in position 2 and 6 with thienyl groups, have strong absorptions in the visible and near infrared (NIR), thus allowing the production of photovoltaic devices, for example photovoltaic cells, capable of more efficiently exploiting solar radiation.

Thanks to the above-reported characteristics, efforts of scientific community towards the development of both new tetracarboxynaphthalenediimide compounds and new processes for their preparation, are greatly encouraged.

N,N'-dialkyl-1,4,5,8-tetracarboxynaphthalenediimide compounds (NDIs) disubstituted in position 2 and 6 with aryl or heteroaryl groups can generally be prepared by means of a Stille reaction or of a Suzuki reaction starting from 2,6-dihalogen-1,4,5,8-tetracarboxy-naphthalene-N,N'-dialkyldiimide which can be prepared through a two-step process starting from 1,4,5,8-tetracarboxynaphthalenedianhydride (NDA). In the first step, the halogenation of 1,4,5,8-tetracarboxynaphthalenedianhydride (NDA) is generally carried out to give 2,6-dihalogen-1,4,5,8-naphthalenedianhydride which, in the second step, by treatment with a primary amine, is transformed into the corresponding diimide.

The halogenation reaction of 1,4,5,8-tetracarboxynaphthalenedianhydride (NDA) can be carried out according to methods described in literature such as, for example:

reaction of 1,4,5,8-tetracarboxynaphthalene-dianhydride (NDA) with dibromoisocyanuric acid in the presence of sulfuric acid, at 130° C., for 15 hours, as described by Chaignon F. at al. in the article: "Very large acceleration of the photoinduced electron transfer in a Ru(bpy)$_3$-naphthalene bisimide dyad bridged on the naphthyl core", *Chemical Communications* (2007), pages 64-66);

reaction of 1,4,5,8-tetracarboxynaphthalene-dianhydride (NDA) with dibromoisocyanuric acid, in the presence of oleum in a quantity higher than 20%, at room temperature, for 4 hours, as described in American patent application US 2008/0300405;

reaction of 1,4,5,8-tetracarboxynaphthalene-dianhydride (NDA) with bromine and iodine, in the presence of oleum, at 95° C., for 24 hours, under a nitrogen stream, as described in international patent application WO 2007/146250;

reaction of 1,4,5,8-tetracarboxynaphthalene-dianhydride (NDA) with bromine and iodine, in the presence of oleum, at room temperature, overnight, as described by Piyakulawat P. et al. in the article: "Synthesis and preliminary characterization of novel naphthalene bisimide based copolymers", *Synthetic Metals* (2009), Vol. 159, pages 467-472.

Subsequently, the 2,6-dihalogen-1,4,5,8-tetra-carboxynaphthalenedianhydride is transformed into the corresponding diimide following methods described in literature, such as, for example:

reaction of 2,6-dibromo-1,4,5,8-tetra-carboxynaphthalenedianhydride with a primary amine (e.g., 2-ethylhexylamine), in the presence of acetic acid, at 120° C., as described by Guo X. et al. in the article: "Conjugated Polymers from Naphthalene Bisimide", *Organic Letters*, (2008), Vol. 10 (23), pages 5333-5336;

reaction of 2,6-dibromo-1,4,5,8-tetra-carboxynaphthalenedianhydride with a primary amine (e.g., n-octylamine) in the presence of acetic acid and N-methylpyrrolidone, at 85° C. for 6 hours under a stream of nitrogen, as described in international patent application WO 2007/146250;

reaction of 2,6-dibromo-1,4,5,8-tetracarboxy-naphthalenedianhydride with a primary amine (e.g., 2-octyldodecylamine) in the presence of a mixture of propionic acid and o-xylene, at 140° C., for 2 hours, as described by Chen Z. et al. in the article "Naphthalenedicarboximide-vs Perylene-dicarboximide-Based Copolymers. Synthesis and Semiconducting Properties in Bottom-Gate N-Channel Organic Transistors", *Journal of the American Chemical Society* (2009), Vol. 131, pages 8-9;

reaction of 2,6-dichloro-1,4,5,8-tetra-carboxynaphthalenedianhydride with a primary amine (e.g., n-octylamine) in the presence of glacial acetic acid, at 140° C., for 2 hours, as described by Thalacker C. et al. in the article: "Synthesis and Optical and Redox Properties of Core-Substituted Naphthalene Diimide Dyes", *Journal of Organic Chemistry*, (2006), Vol. 71 (21), pages 8098-8105.

In the case of the Stille reaction, the N,N'-dialkyl-1,4,5,8-tetracarboxynaphthalenediimide compounds (NDIs) disubstituted in position 2 and 6 with aryl or heteroaryl groups, can be prepared by the reaction of 2,6-dihalogen-1,4,5,8-tetracarboxy-naphthalene-N,N'-dialkyldiimide with a tributylstannyl-arene or with a tributylstannylheteroarene.

In the case of the Suzuki reaction, the N,N'-dialkyl-1,4,5,8-tetracarboxynaphthalendiimide(NDIs) compounds disubstituted in position 2 and 6 with aryl or heteroaryl groups, can be prepared by reaction of 2,6-dihalogen-1,4,5,8-tetracarboxynaphthalene-N,N'-dialkyldiimide with the ester of 2-arylboronic acid or with the ester of 2-heteroarylboronic acid.

Both of the above Stille and Suzuki reactions are carried out in the presence of catalysts containing palladium, in the presence of solvents such as, for example, toluene, xylene, 1,2-dimethoxyethane, tetrahydrofuran, dimethylsulfoxide, N,N-dimethyl-formamide, 1,4-dioxane, at a temperature ranging from 80° C. to 130° C., for a time ranging from 12 to 24 hours.

Examples of the above Stille and Suzuki reactions are described in the art.

Piyakulawat P. et al., for example, in the article "Low band gap copolymers containing naphthalene-1,4,5,8-tetracarboxylic bisimide: Synthesis, properties and organic solar cell applications", *Synthetic Metals* (2011), Vol. 161, No. 18, pages 1238-1244, describe a process for the preparation of 2,6-di-(2,2'-thienyl)-N,N'-diethylhexyl-1,4,5,8-tetracarboxynaphthalenediimide [formula (Ia) wherein R=ethylhexyl] as reported in the following Scheme 1:

Scheme 1

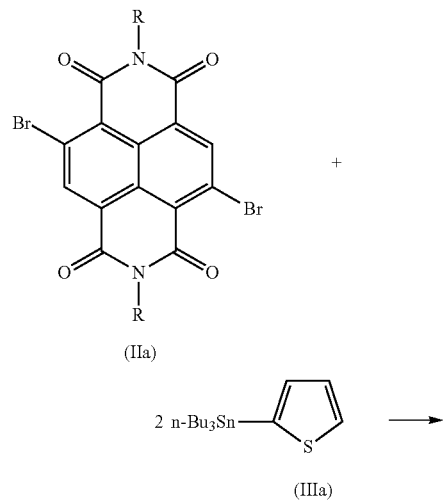

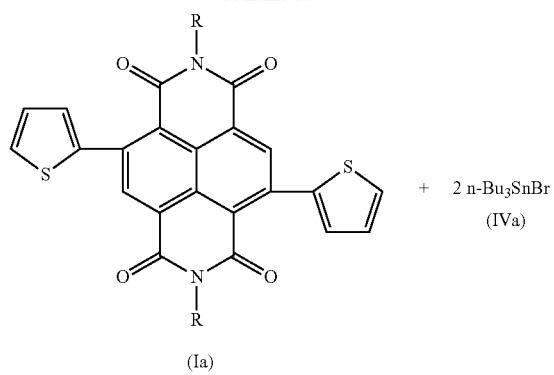

wherein 2,6-dibromo-N,N'-diethylhexyl-1,4,5,8-tetra-carboxynaphthalenediimide [formula (IIa) wherein R=ethylhexyl] is reacted with 2-tri-n-butylstannylthiophene [formula (IIIa)], in the presence of anhydrous toluene, at reflux temperature, under a stream of argon, overnight. At the end of the reaction, after adding an aqueous solution of hydrochloric acid 2 N, extraction is carried out with chloroform. After washing the organic phase to neutrality with water and anhydrification on sodium sulfate, the solvent is removed by distillation at reduced pressure, obtaining, after purification by means of crystallization from ethanol, 2,6-di-(2,2'-thienyl)-N,N'-diethylhexyl-1,4,5,8-tetracarboxynaphthalenediimide with a yield of 92%.

In the article: "Synthesis and preliminary characterization of novel naphthalene bisimide based copolymers", *Synthetic Metals* (2009), Vol. 159, pages 467-472, reported above, Piyakulawat P. et al. describe a process for the preparation of 2,6-di-(2,2'-thienyl)-N,N'-dihexyl-1,4,5,8-tetracarboxynaphthalene-diimide [formula (Ib) wherein $R_1$=hexyl] as reported in the following Scheme 2:

Scheme 2

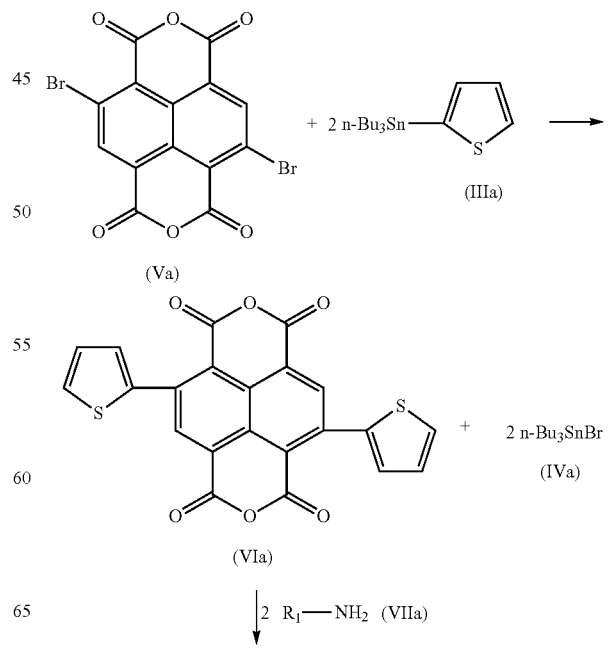

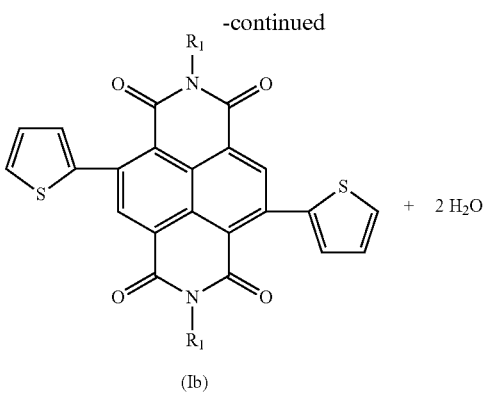

(Ib)

wherein 2,6-dibromo-1,4,5,8-tetracarboxynaphthalene dianhydride [formula (Va)] is reacted with 2-tri-n-butylstannyl thiophene [formula (IIIa)], in the presence of anhydrous toluene, at reflux temperature, for 15 hours, in the presence of bis(triphenylphosphine)palladium(II)chloride [PdCl$_2$(PPh$_3$)$_2$] as catalyst, in quantities equal to 3 moles per 100 moles of the starting 2,6-dibromo-1,4,5,8-tetracarboxynaphthalenedianhydride [formula (Va)]. At the end of the reaction, after adding an aqueous solution of hydrochloric acid 2 N, extraction is carried out with chloroform. After washing the organic phase to neutrality with water and after anhydrification with sodium sulfate, the solvent is removed by distillation at reduced pressure, obtaining, after purification by washing with hexane and crystallization from methanol, 2,6-di-(2,2'-thienyl)-1,4,5,8-tetracarboxynaphthalenedianhydride [formula (VIa)] with a yield equal to 41%. Subsequently, the 2,6-di-(2,2'-thienyl)-1,4,5,8-tetracarboxynaphthalene-dianhydride [formula (VIa)] is reacted with n-hexylamine [formula (VIIa) wherein R$_1$=hexyl], at 150° C., under a stream of argon, for 5 hours. At the end of the reaction, after adding an aqueous solution of hydrochloric acid 2 N, extraction is carried out with chloroform. After washing the organic phase to neutrality with water and after anhydrification, the solvent is removed by distillation at reduced pressure, obtaining, after purification by means of elution on a chromatographic column of silica gel (eluent: chloroform), 2,6-di-(2,2'-thienyl)-N,N'-dihexyl-1,4,5,8-tetracarboxynaphthalenediimide [formula (Ib) wherein R$_1$=hexyl] with a yield of 23%.

The 2-tri-n-butylstannylthiophene [formula (IIIa)] used in the above processes, is a commercial product, generally prepared starting from thiophene, n-butyl-lithium and tri-n-butylstannylchloride through a two-step process as resorted in the following scheme 3:

Scheme 3

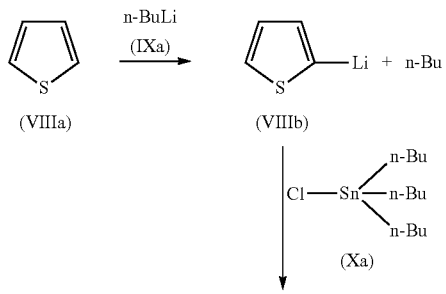

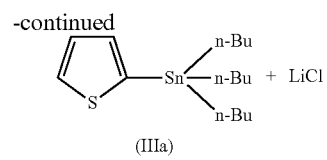

(IIIa)

wherein thiophene [formula (VIIIa)] is reacted with n-butyl-lithium [formula (IXa)] to give 2-thienyl-lithium [formula (VIIIb)] which is reacted, in situ, with tributyl stannyl chloride [formula (Xa)] giving 2-tri-n-butyl stannyl thiophene [formula (IIIa)].

The above process has various drawbacks, such as, for example:
- use of organic derivatives of lithium, highly flammable substances which must be handled with care and with the absolute absence of oxygen and of humidity;
- use of the tin derivatives, highly toxic substances for human beings and harmful for the environment.

It is known that instead of 2-tri-n-butylstannylthiophene, the ester of 2-thienylboronic acid, also a commercial product, can be used, which is generally prepared starting from thiophene, with n-butyl-lithium and triester of boronic acid through a two-step process as reported in the following Scheme 4:

Scheme 4

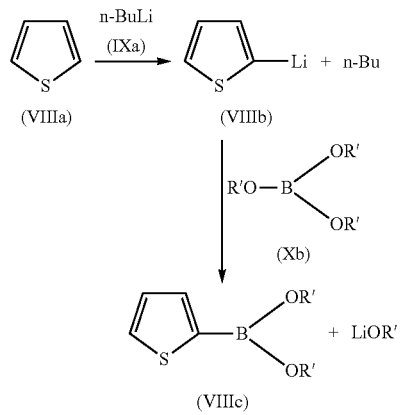

wherein thiophene [formula (VIIIa)] is reacted with n-butyl-lithium [formula (IXa)] to give 2-thienyl-lithium [formula (VIIIb)] which is reacted in situ with a triester of boronic acid [formula (Xb)] wherein B=boron; R', equal to or different from each other, represent a hydrogen atom, or a linear or branched C$_1$-C$_{20}$ alkyl group; or the substituents R', together with the other atoms to which they are bound, can form a heterocyclic ring having formula (IV):

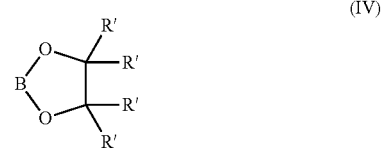

wherein B=boron; R', equal to or different from each other, represent a hydrogen atom, or a linear or branched C$_1$-C$_{20}$ alkyl group, obtaining the ester of 2-thienylboronic acid [formula (VIIIc)].

The above process however also has various drawbacks, such as, for example:
- use of organic derivatives of lithium, highly flammable substances which must be handled with care and with the complete absence of oxygen and of humidity;
- use of trialkyl esters of boronic acid which often have problems linked to their purification with low yields of the end-product.

It should also be noted that the above processes for the preparation of 2,6-di-(2,2'-thienyl)-N,N'-di-alkyl-1,4,5,8-tetracarboxynaphthalenediimide reported above, can have various drawbacks, such as, for example:
- use of derivatives of tin, toxic substances for human beings and harmful for the environment;
- use of organic derivatives of lithium, highly flammable substances which must be handled with care and with the complete absence of oxygen and of humidity;
- relatively long times, ranging from a few hours and a few tens of hours (normally from 3 hours to 24 hours);
- use of an excess of 2-tri-n-butylstannyl-thiophene (IIIa) in order to obtain high yields of end-product, with consequent higher production costs and wastewater disposal costs;
- use of 2-tri-n-tributylstannylthiophene (IIIa) which creates problems due to the fact that for each mole of 2,6-di-(2,2'-thienyl)-N,N'-dialkyl-1,4,5,8-tetracarboxynaphthalenediimide obtained, two moles of tri-n-butyl-stannyl-bromide (IVa) are formed (as reported above in Scheme 1 and Scheme 2), which must be suitably disposed of with a consequent increase in the process costs;
- relatively high quantities of catalyst used, as normally a quantity of catalyst containing palladium not lower than 0.5 moles per 100 moles of 2,6-dibromo-1,4,5,8-tetracarboxy-naphthalene starting derivative, is used (these quantities, even if small in absolute terms, are in any case high considering the cost of palladium or its complexes, as it is not always possible to prepare the complexes in situ).

The development of new processes for the preparation of tetracarboxynaphthalenediimide compounds disubstituted with heteroaryl groups capable of overcoming the above drawbacks, is consequently of current interest.

Systems are described in literature, for example, for forming aryl-aryl (Ar—Ar) bonds without the use of tin or boron derivatives. Said reactions, known as direct arylation of aromatic systems, are normally carried out by reacting an aryl halide (Ib) with an aryl or heteroaryl compound (IIb), as reported in the following Scheme 5:

Scheme 5

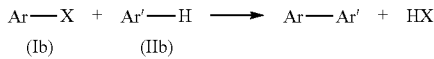

wherein X represents a chlorine, bromine or iodine atom in the presence of a catalyst containing palladium and, in some cases, in the presence of phosphines as ligands of the catalyst containing palladium.

Tamba S. et al., for example, in the article "Palladium-Catalyzed C—H Functionalization of Heteroarenes with Aryl Bromides and Chlorides", *Journal of Organic Chemistry* (2010), Vol. 75 (20), pages 6998-7001, describe an arylation reaction according to Scheme 5 reported above, wherein Ar' is a thiophene, in the presence of a catalyst containing palladium such as, for example, bis(tri-tert-butylphosphine) palladium(II) ([Pd(P-t-Bu$_3$)$_2$]), of a solvent such as, for example, dimethylformamide (DMF) and of a strong base such as, for example, lithium tert-butylate (LiO-t-Bu), at a temperature of 100° C., for 15 hours.

In the article "Ligand-less palladium-catalyzed direct 5-arylation of thiophenes at low catalyst loadings", *Green Chemistry* (2009), Vol. 11, pages 425-432, Roger J. et al. describe an arylation reaction according to Scheme 5 reported above, wherein Ar' is a thiophene substituted in position 2, in the presence of a catalyst containing palladium, such as, for example, palladium(II)acetate ([Pd(OAc)$_2$]), of a solvent such as, for example, dimethylacetamide (DMAc) and of a base such as, for example, potassium acetate (KOAc), at a temperature of 150° C., for 20 hours.

In the article "Palladium-catalyzed direct arylation of thiophenes tolerant silyl groups", *Chemical Communication* (2011), Vol. 47, pages 1872-1874, Chen L. et al. describe an arylation reaction according to Scheme 5 reported above, wherein Ar' is a thiophene substituted in position 2 with a (R)$_3$Si group wherein R can be an alkyl group (e.g., a methyl group), in the presence of a catalyst containing palladium such as, for example, palladium(II)acetate ([Pd(OAc)$_2$]) associated with diphenylphosphinebutane (dppb) as ligand, of a solvent such as, for example, dimethylacetamide (DMAc) and of a base such as, for example, potassium acetate (KOAc), at a temperature of 120° C., for a time ranging from 1 hour to 48 hours.

In the article: "Mechanistic Analysis of Azine N-Oxide Direct Arylation: Evidence for a Critical Role of Acetate in the Pd(OAc)$_2$ Precatalyst", *Journal of Organic Chemistry* (2010), Vol. 75 (23), pages 8180-8189, Sun H. Y. et al. describe various reaction mechanisms for direct mono-arylation, basically distinguishing three types of direct arylation on the basis of the nature of the arene under examination, which can be: a) electron-rich, b) electron-neutral and c) electron-poor. In all cases the presence of palladium (II) acetate ([Pd(OAc)$_2$]) is of crucial importance.

The processes reported above, however, can have various critical aspects, such as, for example:
- use of aryl or heteroaryl compounds, in particular thiophene, substituted in position 2 and, consequently, the necessity of subjecting the end-product to further treatment (e.g., deprotection) in order to obtain the desired product, and the impossibility of using the product obtained as precursor of monomeric units in the preparation of semiconductor polymers;
- use of strong bases (e.g., lithium tert-butylate (LiO-t-Bu)) and, consequently, difficulty in handling said bases, an increase in the possibility of damage with respect to both the health of the operators and to the environment, and higher disposal costs;
- relatively high temperatures and long reaction times and, consequently, higher energy costs and longer process times which can cause degradation of the product obtained.

The Applicant has therefore considered the problem of finding a process for the preparation of a tetra-carboxynaphthalenediimide compound disubstituted with heteroaryl groups, capable of overcoming the drawbacks reported above. In particular, the Applicant has considered the problem of finding a process for the preparation of a tetracarboxynaphthalenediimide compound disubstituted with heteroaryl groups, through direct arylation, more specifically through a double direct arylation, of a tetracarboxynaphthalenediimide compound.

The Applicant has now found that the preparation of a tetracarboxynaphthalenediimide compound disubstituted with heteroaryl groups, can be carried out through a process comprising a double direct arylation of a disubstituted tetracarboxynaphthalenediimide compound, more specifically through a process comprising the reaction of at least one disubstituted N,N'-dialkyl-1,4,5,8-tetracarboxynaphthalenediimide with at least one heteroaryl compound.

There are numerous advantages in operating according to the above process, such as, for example:

- reduction in the process steps with a consequent reduction in the process times and lower production costs;
- non-use of substances toxic for human beings and harmful for the environment such as tin derivatives and highly flammable substances such as lithium alkyls;
- possibility of functionalizing the product obtained to allow it to be used, for example, in (co)polymerizations;
- relatively low temperatures and low reaction times with lower energy costs and lower process times in order to avoid the possible degradation of the product obtained;
- greater safety conditions (e.g., absence of strong bases), with respect to both the health of the operators and the environment.

Said tetracarboxynaphthalenediimide compound disubstituted with heteroaryl groups can be advantageously used as monomer in the synthesis of semiconductor polymers which can be advantageously used in the construction of organic field effect transistors (OFET) or of organic thin film transistors (OTFT)). Furthermore, said tetracarboxynaphthalenediimide compound disubstituted with heteroaryl groups can be advantageously used as monomer in the synthesis of semiconductor polymers which can be advantageously used in the construction of photovoltaic devices such as, for example photovoltaic cells, photovoltaic modules, solar cells, solar modules, on both rigid and flexible supports. In addition, said tetracarboxy-naphthalenediimide compound disubstituted with heteroaryl groups has a good thermal stability, good properties as electron-acceptor compound, a good processability in organic solvents normally used in the construction of the above-mentioned transistors or of the above-mentioned photovoltaic devices.

An object of the present invention therefore relates to a process for the preparation of a tetracarboxy-naphthalenediimide compound disubstituted with heteroaryl groups having general formula (I):

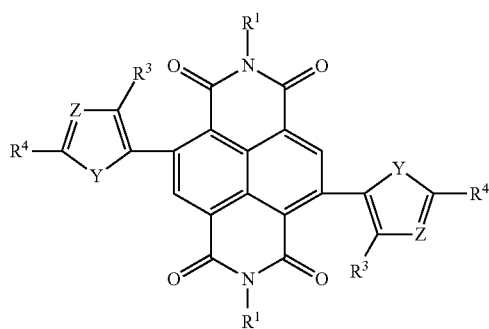

wherein:
- $R^1$ represents a linear or branched $C_1$-$C_{30}$, preferably $C_2$-$C_{20}$, alkyl group;
- Y represents an oxygen atom; a sulfur atom; a group $NR^5$ wherein $R^5$ represents a hydrogen atom, or a linear or branched $C_1$-$C_{20}$, preferably $C_2$-$C_{10}$, alkyl group;
- Z represents a nitrogen atom; or a group $CR^2$ wherein $R^2$ has the meanings below reported;
- $R^3$ represents a hydrogen atom; a linear or branched $C_1$-$C_{20}$, preferably $C_2$-$C_{10}$, alkyl group; a cycloalkyl group optionally substituted; an aryl group optionally substituted; a linear or branched $C_1$-$C_{20}$, preferably $C_2$-$C_{10}$, alkoxyl group; a polyethyleneoxyl group $R^1$—O—[—$CH_2$—$CH_2$—O]$_n$— wherein $R^1$ has the same meaning above reported and n is an integer ranging from 1 to 4; a group —$R^6$—OH wherein $R^6$ represents a linear or branched $C_1$-$C_{20}$, preferably $C_2$-$C_{10}$, alkylene group; a group —$R^6$—$OR^7$ wherein $R^6$ has the same meanings above reported and $R^7$ represents a linear or branched $C_1$-$C_{20}$, preferably $C_2$-$C_{10}$, alkyl group, or a polyethyleneoxyl group $R^1$—O—[—$CH_2$—$CH_2$—O]$_n$— wherein $R^1$ has the same meaning above reported and n is an integer ranging from 1 to 4; a group —$COR^1$ wherein $R^1$ has the same meanings above reported; a group —$COOR^1$ wherein $R^1$ has the same meanings above reported; a —CHO group; a cyano group (—CN);
- $R^2$ represents a hydrogen atom; a linear or branched $C_1$-$C_{20}$, preferably $C_2$-$C_{10}$, alkyl group; or, when $R^3$ is different from hydrogen or when $R^3$=$R^2$, it represents a linear or branched $C_1$-$C_{20}$, preferably $C_2$-$C_{10}$, alkoxyl group;
- or $R^3$ and $R^2$ can be optionally bound to each other so as to form, together with the carbon atoms to which they are bound, a cycle or polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;
- $R^4$ represents a hydrogen atom; a linear or branched $C_1$-$C_{20}$, preferably $C_2$-$C_{10}$, alkyl group; a cycloalkyl group optionally substituted; an aryl group optionally substituted; a heteroaryl group optionally substituted; a —CHO group; a group —$COR^1$ wherein $R^1$ has the same meanings above reported; a group —$COOR^1$ wherein $R^1$ has the same meanings above reported; a group —$CONR^2$ wherein $R^2$ has the same meanings above reported; a cyano group (—ON);
- or $R^2$ and $R^4$ can be optionally bound to each other so as to form, together with the carbon atoms to which they are bound, a cycle or polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

said process comprising reacting at least one disubstituted N,N'-dialkyl-1,4,5,8-tetracarboxy-naphthalenediimide having general formula (II):

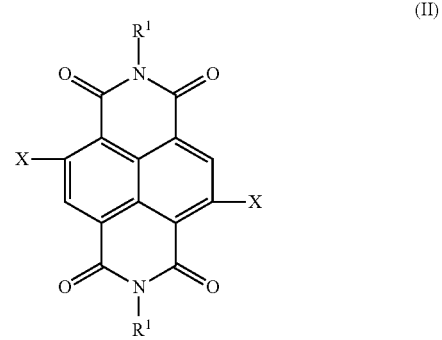

wherein X represents a halogen atom selected from chlorine, bromine, iodine, preferably bromine; $R^1$ has the same meanings above reported;
with at least one heteroaryl compound having general formula (III):

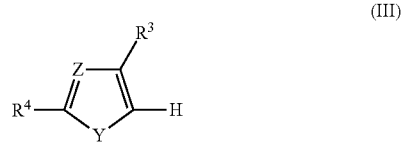

wherein Y, Z, $R^3$ and $R^4$, have the same meanings above reported.

For the purposes of the present description and of the following claims, the definitions of the numerical ranges always comprise the extremes unless otherwise specified.

The term "$C_1$-$C_{30}$ alkyl group" or "$C_1$-$C_{20}$ alkyl group" refers to a linear or branched alkyl group having from 1 to 30 carbon atoms or from 1 to 20 carbon atoms, respectively. Specific examples of a $C_1$-$C_{30}$ or $C_1$-$C_{20}$ alkyl group are: methyl, ethyl, n-propyl, iso-propyl, n-butyl, iso-butyl, tert-butyl, pentyl, ethyl-hexyl, hexyl, n-heptyl, octyl, nonyl, decyl, dodecyl, dodecyloctyl.

The term "$C_1$-$C_{20}$ alkylene group" refers to a linear or branched alkylene group having from 1 to 20 carbon atoms. Specific examples of a $C_1$-$C_{20}$ alkylene group are: methylene, ethylene, n-propylene, iso-propylene, n-butylene, iso-butylene, tert-butylene, pentylene, ethyl-hexylene, hexylene, heptylene, octylene, nonylene, decylene, dodecylene.

The term "cycloalkyl group" means a cycloalkyl group having from 3 to 10 carbon atoms. Said cycloalkyl group can be optionally substituted by one or more groups, equal to or different from each other, selected from: halogen atoms; hydroxyl groups; $C_1$-$C_{20}$ alkyl groups; $C_1$-$C_{20}$ alkoxyl groups; cyano groups; amino groups; nitro groups. Specific examples of a cycloalkyl group are: cyclopropyl, 2,2-difluorocyclopropyl, ciclobutyl, ciclopentyl, ciclohexyl, methylcyclohexyl, methoxycyclohexyl, fluorocyclohexyl, phenylcyclohexyl.

The term "aryl group" means an aromatic carbocyclic group. Said aromatic carbocyclic group can be optionally substituted with one or more groups, equal to or different from each other, selected from: halogen atoms such as, for example, fluorine, chlorine, bromine, preferably fluorine; hydroxyl groups; $C_1$-$C_{20}$ alkyl groups; $C_1$-$C_{20}$ alkoxyl groups, cyano groups; amino groups; nitro groups. Specific examples of an aryl group are: phenyl, methylphenyl, trimethylphenyl, methoxyphenyl, hydroxyphenyl, phenyloxyphenyl, fluorophenyl, pentafluorophenyl, nitrophenyl, dimethylaminophenyl, naphthyl, phenylnaphthyl, phenanthrene, anthracene.

The term "$C_1$-$C_{20}$ alkoxyl group" means a linear or branched alkoxyl group having from 1 to 20 carbon atoms. Specific examples of a $C_1$-$C_{20}$ alkoxyl group are: methoxyl, ethoxyl, n-propoxyl, iso-propoxyl, n-butoxyl, iso-butoxyl, tert-butoxyl, pentoxyl, hexyloxyl, heptyloxyl, octyloxyl, nonyloxyl, decyloxyl, dodecyloxyl.

The term "polyethyleneoxyl group" means a group having oxyethylene units in the molecule. Specific examples of a polyethyleneoxyl group are: methyloxy-ethyleneoxyl, methyloxy-diethyleneoxyl, 3-oxatetraoxyl, 3,6-dioxaheptyloxyl, 3,6,9-trioxadecyloxyl, 3,6,9,12-tetraoxahexadecyloxyl.

The term "heteroaryl group" means an aromatic heterocyclic group, penta- or hexa-atomic, also benzocondensed or heterobicyclic, containing from 1 to 4 heteroatoms selected from nitrogen, oxygen, sulfur, silicon, selenium, phosphorus. Specific examples of a heteroaryl group are: pyridine, methylpyridine, methoxypyridine, phenylpyridine, fluoropyridine, pyrimidine, pyridazine, pyrazine, triazine, tetrazine, quinoline, quinazoline, furan, thiophene, hexylthiophene, pyrrole, oxazole, thiazole, isooxazole, isothiazole, oxadiazole, thiadiazole, pyrazole, imidazole, triazole, tetrazole, indole, benzofuran, benzothiophene, benzooxazole, benzothiazole, triazolepyridine, triazolepyrimidine, coumarin.

The term "cycle or polycyclic system" means a system containing one or more rings containing from 3 to 14 carbon atoms, optionally containing heteroatoms selected from nitrogen, oxygen, sulfur, silicon, selenium, phosphorus. Specific examples of a cycle or polycyclic system are: thiadiazole, benzothiophene, quinoxaline, pyridine.

The above process can be carried out according to the following scheme:

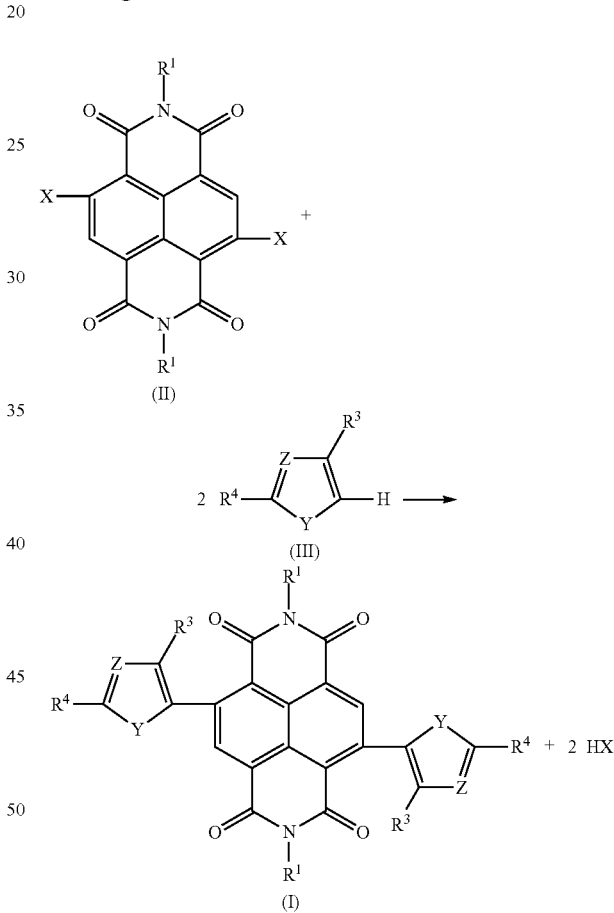

wherein X, Y, Z, $R^1$, $R^3$ and $R^4$, have the same meanings described above.

According to a particularly preferred embodiment of the present invention, said process relates to the preparation of 2,6-di-(2,2'-thienyl)-N,N'-dialkyl-1,4,5,8-tetracarboxynaphthalenediimide corresponding to a tetracarboxynaphthalenediimide compound disubstituted, in positions 2 and 6, with heteroaryl groups having general formula (I) wherein $R^1$ represents an ethyl-hexyl group or a n-heptyl group, Y represents a sulfur atom, Z represents a group $CR^2$ wherein $R^2$ represents a hydrogen atom, and $R^3$ and $R^4$, represent a hydrogen atom.

According to a preferred embodiment of the present invention, said disubstituted N,N'-dialkyl-1,4,5,8-tetracarboxynaphthalenediimide having general formula (II) and said heteroaryl compound having general formula (III) can be used in molar ratios ranging from 1:2 to 1:20, preferably ranging from 1:4 to 1:12.

According to a preferred embodiment of the present invention, said process can be carried out in the presence of at least one weak organic base.

According to a preferred embodiment of the present invention, said weak organic base can be selected, for example, from: carbonates of alkaline metals (e.g., lithium, sodium, potassium, caesium) or of alkaline-earth metals (e.g., magnesium, calcium) such as, for example, lithium carbonate, potassium carbonate, sodium carbonate, caesium carbonate, magnesium carbonate, calcium carbonate, or mixtures thereof. Said weak organic base is preferably potassium carbonate.

According to a preferred embodiment of the present invention, said disubstituted N,N'-dialkyl-1,4,5,8-tetracarboxynaphthalenediimide having general formula (II) and said weak organic base can be used in molar ratios ranging from 1:2.2 to 1:20, preferably ranging from 1:2.5 to 1:4.

According to a preferred embodiment of the present invention, said process can be carried out in the presence of at least one weak organic acid.

According to a preferred embodiment of the present invention, said weak organic acid can be selected, for example, from: acetic acid, propionic acid, pivalic acid, isobutyl acid, or mixtures thereof. Said weak organic acid is preferably pivalic acid.

According to a preferred embodiment of the present invention, said disubstituted N,N'-dialkyl-1,4,5,8-tetracarboxynaphthalenediimide having general formula (II) and said weak organic acid can be used in molar ratios ranging from 100:10 to 100:50, preferably ranging from 100:15 to 100:40.

According to a preferred embodiment of the present invention, said process can be carried out in the presence of at least one catalyst containing palladium.

According to a preferred embodiment of the present invention, said catalyst containing palladium can be selected from: compounds of palladium in oxidation state (0) or (II) such as, for example, palladium(II) chloride [$PdCl_2$], palladium(II) acetate [$Pd(OAc)_2$], palladium(0) bis(dibenzylidene) [Pd(dba)$_2$ wherein dba=$C_6H_5CH$=$CHCOCH$=$CHC_6H_5$], palladium(II) bis(acetonitrile) chloride [$Pd(CH_3CN)_2Cl_2$], or mixtures thereof. Said catalyst containing palladium is preferably palladium(II) acetate [$Pd(OAc)_2$].

According to a preferred embodiment of the present invention, said disubstituted N,N'-dialkyl-1,4,5,8-tetracarboxynaphthalenediimide having general formula (II) and said catalyst containing palladium can be used in molar ratios ranging from 100:0.1 to 100:3, preferably ranging from 100:0.4 to 100:2.

According to a preferred embodiment of the present invention, said process can be carried out in the presence of at least one ligand of the catalyst containing palladium.

According to a preferred embodiment of the present invention, said ligand can be selected, for example, from: triphenylphosphine, tricyclohexylphosphonium tetrafluoroborate, 2-dicyclo-hexylphosphine-2'-(N,N-dimethylamino)-biphenyl (DavePhos), di-tert-butyl(methyl)phosphonium tetrafluoroborate, tri-tert-butyl(methyl)phosphonium tetrafluoroborate, or mixtures thereof. Said ligand is preferably di-tert-butyl(methyl)phosphonium tetrafluoroborate.

According to a preferred embodiment of the present invention, said disubstituted N,N'-dialkyl-1,4,5,8-tetracarboxynaphthalenediimide having general formula (II) and said ligand can be used in molar ratios ranging from 100:1 to 100:10, preferably ranging from 100:3 to 100:6.

According to a preferred embodiment of the present invention, said disubstituted N,N'-dialkyl-1,4,5,8-tetracarboxynaphthalenediimide having general formula (II) can be used in a molar concentration ranging from 0.05 mmoles to 2 mmoles, preferably ranging from 0.1 mmoles to 1.5 mmoles.

According to a preferred embodiment of the present invention, said process can be carried out in the presence of at least one non-polar organic solvent.

According to a preferred embodiment of the present invention, said non-polar organic solvent can be selected, for example, from: toluene, xylene, chlorobenzene, or mixtures thereof. Said non-polar organic solvent is preferably toluene.

According to a preferred embodiment of the present invention, said process can be carried out at a temperature ranging from 80° C. to 170° C., preferably ranging from 100° C. to 150° C.

According to a preferred embodiment of the present invention, said process can be carried out for a time ranging from 30 minutes to 24 hours, preferably ranging from 1 hour to 20 hours.

The disubstituted N,N'-dialkyl-1,4,5,8-tetra-carboxynaphthalenediimide having general formula (II) can be obtained according to processes known in the art, for example, by halogenation of the corresponding N,N'-dialkyl-1,4,5,8-tetracarboxynaphthalenedianhydride and subsequent diamidation reaction. Greater details relating to these processes can be found, for example, in international patent application WO 2007/146250; or in the article of Chaignon F. et al.: "Very large acceleration of the photoinduced electron transfer in a Ru(bpy)-3-naphthalene bisimide dyad bridged on the naphthyl core", *Chemical Communications* (2007), pages 64-66; or in the article of Thalacker C. et al.: "Synthesis and Optical and Redox Properties of Core-Substituted Naphthalene Diimide Dyes", *Journal of Organic Chemistry*, (2006), Vol. 71 (21), pages 8098-8105.

The heteroaryl compound having general formula (III) can be easily found on the market.

The analysis and characterization methods reported hereunder were used.

$^1$H-NMR Spectroscopy

The $^1$H-NMR spectra of the tetracarboxy-naphthalenediimide compounds disubstituted with heteroaryl groups object of the present invention, were registered by means of a nuclear magnetic resonance spectrometer Bruker Avance 400, at a temperature of 25° C., using deuterated chloroform ($CDCl_3$). The signal of the solvent used [i.e. deuterated chloroform ($CDCl_3$)] set at 7.26 ppm was used as reference for the chemical shifts.

Solutions of the tetracarboxynaphthalenediimide compounds disubstituted with heteroaryl groups object of the present invention, having concentrations equal to 5 mg-10 mg of tetracarboxynaphthalenediimide compound disubstituted with heteroaryl groups to be analyzed in 0.75 ml of solvent, were used for the purpose.

Mass Spectra

The mass spectra of the tetracarboxy-naphthalenediimide compounds disubstituted with heteroaryl groups were carried out with an inverse geometry double-focusing spectrometer AT 95S in DCI ("Desorption Chemical Ionization") with iso-butane as reagent gas in positive ion modality. The emission current of the filament was calibrated at 0.1 mA with an electron beam energy equal to 100 eV and with a temperature of the ion source maintained at 90° C.

Some illustrative and non-limiting examples are provided hereunder for a better understanding of the present invention and for its embodiment.

EXAMPLE 1

Preparation of 2,6-di-(2,2'-thienyl)-N,N'-di-(2-ethyl-hexyl)-1,4,5,8-tetracarboxynaphthalenediimmide having formula (a)

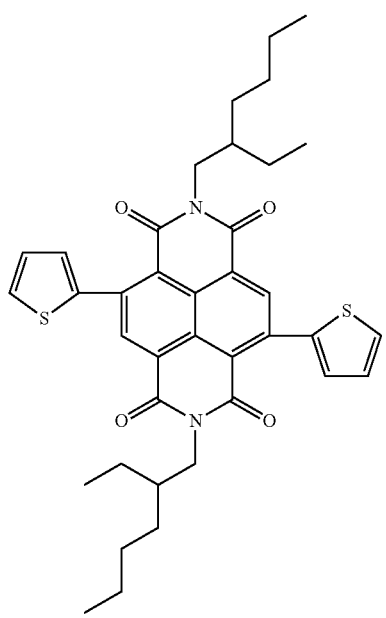

(a)

2,6-dibromonaphthalene-1,4,5,8-tetracarboxy-N,N'-di(2-ethyl-hexyl)imide (0.324 g, 0.5 mmoles), potassium carbonate (0.207 g, 1.5 mmoles), pivalic acid (15 mg, 0.15 mmoles), anhydrous toluene (5 ml), thiophene (0.421 g, 5 mmoles) and palladium (II) acetate [Pd(OAc)$_2$] (1.2 mg, 0.005 mmoles), were charged into a 10 ml Pyrex glass reactor equipped with a screw stopper.

The reactor was placed in an oil bath preheated to 120° C. and left under vigorous stirring for 18 hours. After cooling to room temperature (25° C.), the reaction mixture was put in a saturated solution of sodium chloride (25 ml) and extracted with ethyl acetate (3×25 ml). The organic phase obtained was dried on anhydrous sodium sulfate and evaporated. The residue obtained (brown solid) was purified by flash chromatography on silica gel using toluene as eluent, obtaining 262 mg of pure 2,6-di-(2,2'-thienyl)-N,N'-di-(2-ethyl-hexyl)-1,4,5,8-tetracarboxynaphthalenediimmide as a red solid (yield 80%).

Said 2,6-di-(2,2'-thienyl)-N,N'-di-(2-ethyl-hexyl)-1,4,5,8-tetracarboxynaphthalenediimmide was characterized by means of $^1$H-NMR (400 MHz, CDCl$_3$) obtaining the following spectrum: δ=8.76 (s, 2H), 7.56 (dd, J=5.2, 1.2 Hz, 2H), 7.29 (dd, J=3.2, 1.2 Hz, 2H), 7.19 (dd, J=5.2, 3.2 Hz, 2H), 4.13–4.10 (m, 4H), 1.94–1.88 (m, 2H), 1.38–1.25 (m, 16H), 0.95–0.89 (m, 12H).

Said 2,6-di-(2,2'-thienyl)-N,N'-di-(2-ethyl-hexyl)-1,4,5,8-tetracarboxynaphthalenediimmide was also characterized by means of mass spectrum MS obtaining the following value: m/z: 654.9 (M$^+$).

EXAMPLE 2

Preparation of 2,6-di-(2,2'-thienyl)-N,N'-di-(n-heptyl)-1,4,5,8-tetracarboxynaphthalenediimmide having formula (b)

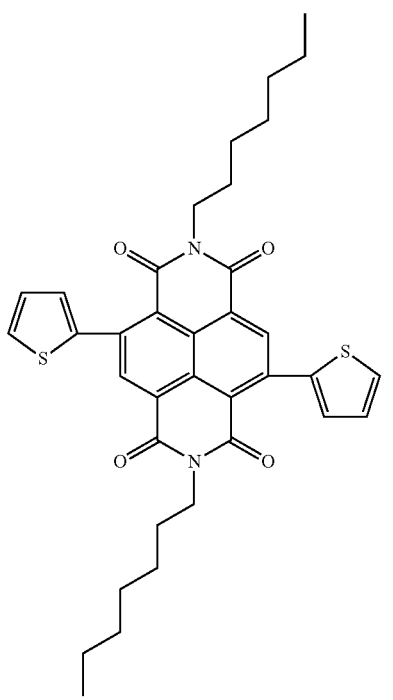

(b)

2,6-dibromonaphthalene-1,4,5,8-tetracarboxy-N,N'-di(n-heptyl)imide (0.310 g, 0.5 mmoles), potassium carbonate (0.207 g, 1.5 mmoles), pivalic acid (15 mg, 0.15 mmoles), anhydrous toluene (5 ml), thiophene (0.421 g, 5 mmoles) and palladium (II) acetate [Pd(OAc)$_2$] (1.2 mg, 0.005 moles), were charged into a 10 ml Pyrex glass reactor equipped with a screw stopper.

The reactor was placed in an oil bath preheated to 120° C. and left under vigorous stirring for 18 hours. After cooling to room temperature (25° C.), the reaction mixture was put in a saturated solution of sodium chloride (25 ml) and extracted with ethyl acetate (3×25 ml). The organic phase obtained was dried on anhydrous sodium sulfate and evaporated. The residue obtained (brown solid) was purified by flash chromatography on silica gel using toluene as eluent, obtaining 266 mg of pure 2,6-di-(2,2'-thienyl)-N,N'-di-(n-heptyl)-1,4,5,8-tetracarboxynaphthalenediimmide as a red solid (yield 85%).

Said 2,6-di-(2,2'-thienyl)-N,N'-di-(n-heptyl)-1,4,5,8-tetracarboxynaphthalenediimmide was characterized by means of $^1$H-NMR (400 MHz, CDCl$_3$) obtaining the following spectrum: δ=8.72 (s, 2H), 7.59 (dd, J=5.2, 1.2 Hz, 2H), 7.29 (dd, J=3.6, 1.2 Hz, 2H), 7.21 (dd, J=5.2, 3.6 Hz, 2H), 4.10–4.07 (m, 4H), 1.69–1.64 (m, 4H), 1.37–1.27 (m, 16H), 0.90–0.86 (m, 6H).

Said 2,6-di-(2,2'-thienyl)-N,N'-di-(n-heptyl)-1,4,5,8-tetracarboxynaphthalenediimmide was also characterized by means of mass spectrum MS obtaining the following value: m/z: 627.2 (M$^+$).

The invention claimed is:

1. A process for preparing a tetracarboxynaphthalenediimide compound disubstituted with heteroaryl groups of formula (I):

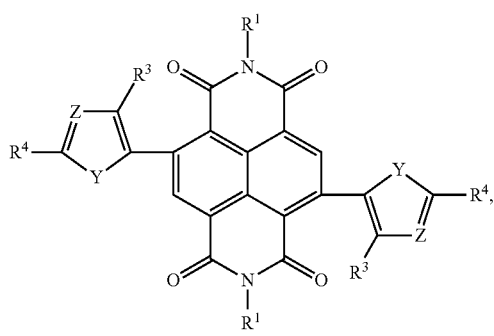

the process comprising:
reacting at least one disubstituted N,N'-dialkyl-1,4,5,8-tetracarboxy-naphthalenediimide of formula (II):

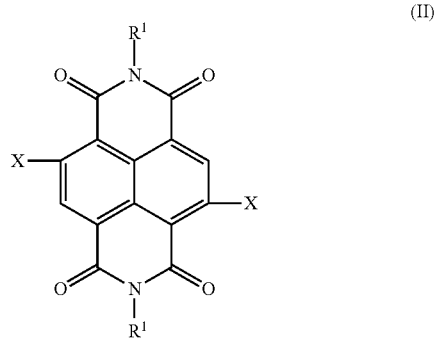

with at least one heteroaryl compound of formula (III):

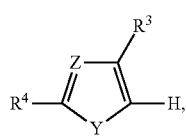

wherein, in formulae (I)-(III),
$R^1$ represents a $C_1$-$C_{30}$ alkyl group;
Y represents an oxygen atom; a sulfur atom; a $NR^5$ group where $R^5$ represents a hydrogen atom; or a $C_1$-$C_{20}$ alkyl group;
Z represents a nitrogen atom; or a $CR^2$ group where $R^2$ is defined below;
$R^3$ represents a hydrogen atom; a linear or branched $C_1$-$C_{20}$ alkyl group; an optionally substituted cycloalkyl group; an optionally substituted aryl group; a linear or branched $C_1$-$C_{20}$ alkoxyl group; a polyethyleneoxyl group $R^1$—O—[—$CH_2$—$CH_2$—O]$_n$— where $R^1$ is defined above and n is an integer of from 1 to 4; a —$R^6$—OH group where $R^6$ represents a linear or branched $C_1$-$C_{20}$ alkylene group; a —$R^6$—O$R^7$ group where $R^6$ is defined above and $R^7$ represents a linear or branched $C_1$-$C_{20}$ alkyl group, or a polyethyleneoxyl group $R^1$—O—[—$CH_2$—$CH_2$—O]$_n$— where $R^1$ is defined above and n is an integer of from 1 to 4; a —$COR^1$ group where $R^1$ is defined above; a —$COOR^1$ group where $R^1$ is defined above; a —CHO group; or a cyano group (—CN);
$R^2$ represents a hydrogen atom; a linear or branched $C_1$-$C_{20}$ alkyl group; or, when $R^3$ is different from hydrogen or when $R^3$=$R^2$, $R^2$ represents a linear or branched $C_1$-$C_{20}$ alkoxyl group;
or $R^3$ and $R^2$ are optionally bound to each other so as to form, together with the carbon atoms to which $R^3$ and $R^2$ are bound, a cycle or polycyclic system containing from 3 to 14 carbon atoms, saturated, unsaturated, or aromatic, optionally containing one or more heteroatoms which are optionally oxygen, sulfur, nitrogen, silicon, phosphorous, and selenium;
$R^4$ represents a hydrogen atom; a linear or branched $C_1$-$C_{20}$ alkyl group; an optionally substituted cycloalkyl group; an optionally substituted aryl group; an optionally substituted heteroaryl group; a —CHO group; a —$COR^1$ group where $R^1$ is defined above; a —$COOR^1$ group where $R^1$ is defined above; a —$CONR^2$ group where $R^2$ is defined above; or a cyano group (—CN);
or $R^2$ and $R^4$ are optionally bound to each other so as to form, together with the carbon atoms to which $R^2$ and $R^4$ are bound, a cycle or polycyclic system containing from 3 to 14 carbon atoms, saturated, unsaturated, or aromatic, optionally containing one or more heteroatoms which are optionally oxygen, sulfur, nitrogen, silicon, phosphorous, and selenium; and
X represents a halogen atom selected from the group consisting of chlorine, bromine, and iodine.

2. The process according to claim 1, wherein said process relates to the preparation of 2,6-di-(2,2'-thienyl)-N,N'-dialkyl-1,4,5,8-tetracarboxynaphthal-enediimide corresponding to a tetracarboxynaphthalenediimide compound disubstituted, in positions 2 and 6, with heteroaryl groups having the formula (I) where
$R^1$ represents an ethyl-hexyl group or a n-heptyl group,
Y represents a sulfur atom,
Z represents a $CR^2$ group where $R^2$ represents a hydrogen atom, and
$R^3$ and $R^4$ represent a hydrogen atom.

3. The process according to claim 1, wherein a molar ratio of said disubstituted N,N'-dialkyl-1,4,5,8-tetracarboxy-naphthalenediimide of formula (II) to said heteroaryl compound of formula (III) is from 1:2 to 1:20.

4. The process according to claim 1, wherein said process is carried out in the presence of at least one weak organic base.

5. The process according to claim 4, wherein said weak organic base is selected from the group consisting of a carbonate of an alkaline metal, a carbonate of an alkaline-earth metal, and any mixture thereof.

6. The process according to claim 4, wherein a molar ratio of said disubstituted N,N'-dialkyl-1,4,5,8-tetracarboxynaphthalenediimide of formula (II) to said weak organic base is from 1:2.2 to 1:20.

7. The process according to claim 1, wherein said process is carried out in the presence of at least one weak organic acid.

8. The process according to claim 7, wherein said weak organic acid is selected from the group consisting of acetic acid, propionic acid, pivalic acid, isobutyl acid, and any mixture thereof.

9. The process according to claim 7, wherein a molar ratio of said disubstituted N,N'-dialkyl-1,4,5,8-tetracarboxynaphthalenediimide of formula (II) to said weak organic acid is from 100:10 to 100:50.

10. The process according to claim 1, wherein said process is carried out in the presence of at least one catalyst containing palladium.

11. The process according to claim 10, wherein said catalyst containing palladium is selected from the group consisting of a compound of palladium in oxidation state (0), a compound of palladium in oxidation state (II), and any mixture thereof.

12. The process according to claim 10, wherein a molar ratio of said disubstituted N,N'-dialkyl-1,4,5,8-tetracarboxynaphthalenediimide of formula (II) to said catalyst containing palladium is from 100:0.1 to 100:3.

13. The process according to claim 10, wherein said process is carried out in the presence of at least one ligand of the catalyst containing palladium.

14. The process according to claim 13, wherein said ligand is selected from the group consisting of triphenylphosphine, tri-cyclohexylphosphonium tetrafluoroborate, 2-di-cyclohexylphosphine-2'-(N,N-dimethyl-amino)-biphenyl, di-tert-butyl(methyl)-phosphonium tetrafluoroborate, tri-tert-butyl (methyl)phosphonium tetrafluoroborate, and any mixture thereof.

15. The process according to claim 13, wherein a molar ratio of said disubstituted N,N'-dialkyl-1,4,5,8-tetracarboxynaphthalenediimide of formula (II) to said ligand is from 100:1 to 100:10.

16. The process according to claim 1, wherein a molar concentration of said disubstituted N,N'-dialkyl-1,4,5,8-tetracarboxynaphthalenediimide of formula (II) is from 0.05 mmoles to 2 mmoles.

17. The process according to claim 1, wherein said process is carried out in the presence of at least one non-polar organic solvent.

18. The process according to claim 17, wherein said non-polar organic solvent is selected from the group consisting of toluene, xylene, chlorobenzene, and any mixture thereof.

19. The process according to claim 1, wherein said process is carried out at a temperature ranging from 80° C. to 170° C.

20. The process according to claim 1, wherein said process is carried out for a time ranging from 30 minutes to 24 hours.

* * * * *

UNITED STATES PATENT AND TRADEMARK OFFICE
CERTIFICATE OF CORRECTION

PATENT NO. : 9,000,170 B2  
APPLICATION NO. : 14/386131  
DATED : April 7, 2015  
INVENTOR(S) : Giuliana Schimperna et al.

Page 1 of 1

It is certified that error appears in the above-identified patent and that said Letters Patent is hereby corrected as shown below:

On the title page, Item (72), the 1st Inventor's First Name is incorrect. Item (72) should read:

--(72)  Inventors:  Giuliana Schimperna, Novara (IT);
Andrea Pellegrino, Trecate (IT);
Stefano Chiaberge, Turin (IT);
Gabriele Bianchi, L'Aquila (IT)--

Signed and Sealed this
Eighteenth Day of August, 2015

Michelle K. Lee
*Director of the United States Patent and Trademark Office*